US008592560B2

(12) United States Patent
Fox

(10) Patent No.: US 8,592,560 B2
(45) Date of Patent: *Nov. 26, 2013

(54) ANTIBODIES TO APICAL INTESTINAL RECEPTORS AND METHODS OF TREATING METABOLIC DISEASE

(75) Inventor: Barbara S. Fox, Wayland, MA (US)

(73) Assignee: Avaxia Biologics, Incorporated, Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/590,755

(22) Filed: Aug. 21, 2012

(65) Prior Publication Data

US 2013/0045213 A1 Feb. 21, 2013

Related U.S. Application Data

(63) Continuation of application No. 12/687,660, filed on Jan. 14, 2010, now Pat. No. 8,268,971, which is a continuation of application No. PCT/US2008/070235, filed on Jul. 16, 2008.

(60) Provisional application No. 60/950,029, filed on Jul. 16, 2007.

(51) Int. Cl.
*C07K 16/00* (2006.01)
*A61K 39/00* (2006.01)

(52) U.S. Cl.
USPC .................. 530/387.1; 530/389.1; 424/157.1

(58) Field of Classification Search
None
See application file for complete search history.

(56) References Cited

PUBLICATIONS

Shojaei A H, "Buccal Mucosa as a route for systemic drug delivery: a review", Journal of Pharmacy and Pharmaceutical Sciences, 1(1):15-30, 1998.
U.S. Appl. No. 13/860,029, co-pending application.
U.S. Appl. No. 13/912,569, co-pending application.

*Primary Examiner* — Robert Landsman
(74) *Attorney, Agent, or Firm* — Darlene A. Vanstone, Esq.; Carolyn S. Elmore, Esq.; Elmore Patent Law Group, P.C.

(57) ABSTRACT

The present invention provides pharmaceutical compositions formulated for direct delivery to the GI tract of a patient comprising an antibody specific for a target apical intestinal receptor. The present invention further provides methods of treating diseases and conditions in a patient comprising administering directly to the GI tract of the patient, compositions of the present invention wherein modulation of the target apical intestinal receptor by the antibody treats the condition.

10 Claims, No Drawings

```
                              SEQUENCE LISTING

<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Ser His Tyr Arg His Val Leu Gly Val Pro Leu Asp Asp Arg Arg Ala
1               5                   10                  15

Cys

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Leu Leu Met Gln Gln Phe Tyr Asn Glu Thr Tyr Tyr Gly Arg Thr Cys
1               5                   10                  15

<210> SEQ ID NO 3
<211> LENGTH: 28
<212> TYPE: PRT
<213> ORGANISM: Artificial Sequence
<220> FEATURE:
<223> OTHER INFORMATION: Synthetic

<400> SEQUENCE: 3

Lys Val Gly Thr Ser Cys Gly Trp Gly Asn Val Phe Gln Val Phe Lys
1               5                   10                  15

Ser Phe Tyr Asn Glu Thr Tyr Phe Glu Arg His Cys
            20                  25

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

His Glu Gly Leu Val Pro Gln His Asp Thr Ser Cys Gln Gln Leu Gly
1               5                   10                  15

Lys

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Glu Glu Ala Gly Leu Arg Ser Arg Thr Arg Pro Ser Ser Pro
1               5                   10
```

```
<210> SEQ ID NO 6
<211> LENGTH: 28
<212> TYPE: PRT
<213> ORGANISM: Artificial Sequence
<220> FEATURE:
<223> OTHER INFORMATION: Synthetic

<400> SEQUENCE: 6

Val Val Leu Ile Ile Gly Cys Cys Pro Gly Gly Thr Ala Ser Asn Ile
1               5                   10                  15

Leu Ala Tyr Trp Val Asp Gly Asp Met Asp Leu Ser
            20                  25
```

ANTIBODIES TO APICAL INTESTINAL RECEPTORS AND METHODS OF TREATING METABOLIC DISEASE

RELATED APPLICATION

This application is a continuation of Ser. No. 12/687,660, filed on Jan. 14, 2010, now U.S. Pat. No. 8,268,971, issued on Sep. 18, 2012, which is a Continuation of International Application No. PCT/US08/70235, which designated the United States and was filed on Jul. 16, 2008, published in English, which claims the benefit of U.S. Provisional Application No. 60/950,029, filed on Jul. 16, 2007. The entire teachings of the above applications are incorporated herein by reference.

FIELD OF THE INVENTION

This invention relates to the modulation of the function of membrane-bound proteins expressed on the luminal surface of the gastrointestinal tract by administration of antibodies specific for such membrane-bound proteins in the form of compositions formulated for delivery directly to the gastrointestinal (GI) tract.

BACKGROUND OF THE INVENTION

The gut responds to a large variety of stimuli, including nutrients, chemicals, mechanical factors, hormones and micro-organisms {Dockray, 2003, J Physiol Pharmacol, 54 Suppl 4, 9-17}. Many of these stimuli are detected through specific receptors that are expressed on the luminal surface of the gastrointestinal tract. In particular, multiple receptors are expressed in the small intestine that recognize sugars.

Sugar transport across the intestinal membranes is tightly regulated and is mediated by a specific set of receptors (reviewed in {Drozdowski and Thomson, 2006, World J Gastroenterol, 12, 1657-70}). Dietary glucose crosses the apical membrane of the enterocyte in the small intestine by the Na+/glucose cotransporter (SGLT1). Dietary fructose is transported across the apical membrane by the facilitative transporter GLUT5. The transporter GLUT2 is important in transporting glucose, particularly at high concentrations {Drozdowski and Thomson, 2006, World J Gastroenterol, 12, 1657-70}. The transporter GLUT7 is also expressed in the small intestine {Li et al., 2004, Am J Physiol Gastrointest Liver Physiol, 287, G236-42}.

GLUT2 expression on the apical surface of enterocytes is regulated by both SGLT1 {Kellett and Brot-Laroche, 2005, Diabetes, 54, 3056-62} and by sweet taste receptors {Mace et al., 2007, J Physiol}. At high glucose concentrations, GLUT2 is inserted into the apical membrane, thereby providing a cooperative mechanism by which glucose absorptive capacity is rapidly and precisely matched to dietary intake immediately after a meal {Mace et al., 2007, J Physiol}. GLUT2 has been identified as a potential therapeutic target for small molecule inhibitors, and quercitin and similar flavonoids have been shown to be GLUT2 inhibitors {Kwon et al., 2007, FASEB J, 21, 366-77}. GLUT2 inhibition could be therapeutic for diabetes and/or obesity.

The intestine expresses taste receptors on the epithelial cells of the stomach and duodenum known as brush cells {Hofer et al., 1996, Proc Natl Acad Sci U S A, 93, 6631-4} {Bezencon et al., 2007, Chem Senses, 32, 41-9}. Taste receptors are also expressed on the enteroendocrine cells of the intestinal tract {Masuho et al., 2005, Chem Senses, 30, 281-90}. The sweet taste receptors (T1Rs), including T1R1, T1R2 and T1R3, belong to the guanine nucleotide regulatory protein (G protein)-coupled receptor (GPCR) superfamily. The receptors have a long extracellular NH2-terminal segment, seven transmembrane a-helices, three extracellular loops, three cytoplasmic loops and a COOH-terminal segment. The T1Rs function as molecular complexes, with the heterodimeric T1R2/T1R3 receptor binding to sweet stimuli while the T1R1/T1R3 complex recognizes amino acids {Rozengurt, 2006, Am J Physiol Gastrointest Liver Physiol, 291, G171-7}.

Polyclonal antibodies have been described that are specific for the receptors present in the GI tract as research agents useful in the detection of the receptor of interest by immunostaining. For example, antibodies have been described to alpha-gustducin, the GTP-binding subunit of taste receptors {Hofer et al., 1996, Proc Natl Acad Sci U S A, 93, 6631-4}. Several antibodies specific for SGLT1, GLUT5, GLUT2, TAS1R1, TAS1R2, TAS1R3 and T2R1 are commercially available as research reagents for the detection of the receptor of interest. However, oral delivery of protein therapeutics to modulate cellular receptors located in the lumen of the GI tract to treat various conditions is an unexplored area. Compositions and methods for administration of therapeutic antibodies directly to the GI tract to target apical intestinal receptors to treat conditions modulated by such target receptors, are therefore needed.

SUMMARY OF THE INVENTION

The present invention provides pharmaceutical compositions formulated for direct delivery to the GI tract of a patient comprising an antibody specific for a target apical intestinal receptor. The present invention further provides methods of treating diseases and conditions in a patient comprising administering directly to the GI tract of the patient compositions of the present invention wherein modulation of the target apical intestinal receptor by the antibody treats the condition.

DETAILED DESCRIPTION OF THE INVENTION

The intestinal tract expresses many different receptors and proteins whose function is to sense and respond to nutrients, microorganisms and other matter contained within the gastrointestinal tract. These receptors and proteins are collectively referred to herein as "apical intestinal receptors". "Apical intestinal receptors" are endogenous transmembrane proteins, expressed in the cell membrane of cells facing the luminal side of the intestinal tract. Classes of apical intestinal receptors described in this invention include but are not limited to: nutrient receptors and transporters (including sugar receptors and transporters, taste receptors, amino acid transporters, and free fatty acid receptors); pattern recognition receptors (including the Toll-like receptors); chemokine and cytokine receptors; bile salt transporters; transporters for calcium iron, and other ions and minerals; peptidases; disaccharidases; growth factor receptors (including epidermal growth factor receptor) and proteins expressed on the surface of cancerous cells in the GI tract. Apical intestinal receptors may be expressed in the stomach, the small intestine or the colon. Preferably, this invention utilizes antibodies directed against apical intestinal receptors expressed in the small intestine or the colon, most preferably those apical intestinal receptors expressed in the small intestine. Apical intestinal receptors may also be expressed in tumors of the gastrointestinal tract.

"Molecular sensing by GI cells plays a critical role in the control of multiple fundamental functions in digestion, including secretory activity of GI glands, absorptive activity, motility, and blood supply of the intestinal tract. Furthermore, molecular sensing of luminal contents also initiates hormonal and/or neural pathways leading to the regulation of caloric intake, pancreatic insulin secretion, and metabolism. Molecular sensing in the GI tract is also responsible for the detection of ingested harmful drugs and toxins, thereby initiating responses critical for survival" (Rozengurt, 2006, Am J Physiol Gastrointest Liver Physiol, 291, G171-7). Many of these responses are mediated by apical intestinal receptors. Antibodies specific for such apical intestinal receptors can be used to inhibit or modulate the function of these receptors including partially blocking at least one biological function of the target receptors.

Accordingly, the present invention provides pharmaceutical compositions formulated for direct delivery to the GI tract of a patient comprising an antibody specific for a target apical intestinal receptor. In one embodiment the target receptor modulates a condition that is treatable by administering an antibody capable of modulating at least one biological function of the target receptor.

As used herein the term "direct delivery to the GI tract of a patient" is oral or rectal delivery to the patient. As used herein the terms "target apical intestinal receptor" and "target receptor" are used interchangeably to refer to an apical intestinal receptor to which an antibody of the invention will selectively bind. The terms "specific for", "selective for" or "selectively binds" when describing the ability of an antibody of the invention to bind to a target apical intestinal receptor means that the antibody can be demonstrated to bind to the target receptor generating a signal greater than that seen from control antibody using any assay known to those experienced in the field, including but not limited to ELISA, RIA, flow cytometry, inhibition or augmentation of biological function, or equilibrium dialysis. The term "receptor" also includes receptors that transmit a signal upon binding the appropriate ligand and receptors that function as transporters.

The GI tract contains receptors specific for sugars. In one embodiment of the invention, antibodies specific to certain target apical intestinal receptors can be used to modulate the uptake of glucose, to treat obesity or diabetes. Such antibodies are selective for apical intestinal receptors that recognize sugars. Such receptors include but are not limited to SGLT1, GLUT5, GLUT2, GLUT7, TAS1R1, TAS1R2, TAS1R3, and T2R1. In one embodiment of the invention, antibodies specific for a sugar receptor can be used to modulate the uptake of sugars such as glucose and fructose, to treat metabolic diseases including but not limited to disease associated with hyperglycemia, diabetes (especially postprandial hyperglycemia), impaired glucose tolerance, impaired fasting glycemia, diabetic complications (e.g., retinopathy, neuropath, nephropathy, ulcer, macroangiopathy), obesity, hyperinsulinemia, hyperlipidemia, hyper-cholesterolemia, hyper-triglyceridemia, lipid metabolism disorder, atherosclerosis, hypertension, congestive heart failure, edema, hyperuricemia, gout or the like. In one embodiment, the antibodies specific for a sugar receptor are delivered orally to the patient. Specific sugar receptors are also present in the lower intestine and in some embodiments it may be preferable to deliver antibodies rectally such as by suppository or similar formulation for direct delivery to the colon. Although not intended to imply a mechanism of action or to limit this invention to antibodies that function with this mechanism, in one embodiment, antibodies specific for sugar receptors in the lumen will block or partially block the binding of sugar to the target receptors and thereby reduce the amount of sugar absorbed from the lumen. Upon ingestion of a meal containing a sugar such as glucose, the amount of glucose absorbed from the lumen of the intestine will be reduced, thus minimizing the caloric intake of the individual and minimizing the postprandial increase in glucose which is detrimental to, for example, diabetic patients. In another embodiment, antibodies specific for sugar receptors may be capable of preventing the development of diabetes or obesity in a patient at high risk of developing diabetes or obesity.

The GI tract expresses receptors that recognize fatty acids and amino acids as well as sugars. Fats are the most effective food group in stimulating endocrine cells of the distal duodenum and jejunum, increasing the secretion of cholesystokinin (CCK), glucose-dependent insulinotropic polypeptide (GIP) and secretin. Glucose stimulates the release of GIP and CCK, but not secretin, in the upper small intestine. The amino acids histidine and arginine stimulate the secretion of GIP, and tryptophan and phenylalanine stimulate CCK. These hormones drive the correct processing of ingested food, by inducing the pancreas to secrete proteolytic enzymes, inducing the secretion of bile to promote the formation of chylomicrons for absorption of triglyceride and long-chain fatty acids, and driving secretion of insulin from the pancreas to facilitate uptake of the absorbed glucose, amino acids, and fat. In one embodiment of this invention, antibodies specific for receptors for fatty acids and amino acids can be used to modulate the release of enteroendocrine hormones in response to ingested food. The fatty acid transporters SMCT1, SMCT2, and MCT1, as well as the G protein coupled receptor (GPCR) GPR40 are involved in fatty acid recognition. Therefore, without being limited to any theory, an antibody specific for SMCT1, SMCT2, MCT1, or the GPCR GPR40 receptor may be capable of inhibiting or partially inhibiting the response to ingested fat. In one embodiment of this invention, antibodies specific for the amino acid carriers EAAC1, EAAT3, PAT1, LYAAT-1, tramdorin 3, $B^{0,+}$, $B^0$, or the di- and tripeptide transporter, PepT1, would be useful in the treatment or prevention of metabolic syndrome, obesity or diabetes or inflammatory diseases, including Crohn's disease, ulcerative colitis, necrotizing enterocolitis, celiac disease, inflammation due to infection with invasive organisms such as *Salmonella* and *Escherichia coli*, or inflammation secondary to injury caused by surgery, trauma, ionizing radiation, or toxic chemicals, including NSAIDs. Other transporters in the GI tract which may serve as targets for the antibodies of the invention include but are not limited to: the multivitamin transporter SMVT which transport, biotin, lipoate and panthothenate among others; the serotonin transporter SERT; the taurine transporter TAUT; the IMINO transporter system; the dicarboxylate transporter NaDC-1; and the nucleoside transporter CNT1.

The GI tract contains receptors that are involved in regulating the response to inflammation. Cells in the GI tract express toll-like receptors (TLRs). TLR1, TLR2, TLR3, TLR4, TLR5, TLR7 and TLR9 are expressed in the small intestine and TLR1, TLR2, TLR3, TLR4, TLR5, TLR6, TLR7, TLR8 and TLR9 are expressed in the epithelium of the large intestine. Stimulation of TLR receptors in the intestine induces the production of chemokines, defensins and CCK {Palazzo et al., 2007, J Immunol, 178, 4296-303}. Antibodies to TLRs may be used to treat inflammatory diseases and disorders of the GI tract, including Crohn's disease, ulcerative colitis, necrotizing enterocolitis, celiac disease, inflammation due to infection with invasive organisms such as *Salmonella* and *Escherichia coli*, or inflammation secondary to injury caused by surgery, trauma, ionizing radiation, or toxic chemicals, including NSAIDs. In one specific embodiment of the invention, antibodies that inhibit signaling through TLR4 are used to treat necrotizing enterocolitis. In one specific embodiment of the invention, antibodies that enhance signaling through TLR2, TLR5 or TLR9 are use to treat intestinal inflammation. It is understood by those skilled in the art that the precise method of treatment of intestinal inflammation by antibodies specific for TLRs will depend on the nature of the inflammation and the characteristics of the patient requiring treatment.

The GI tract contains receptors for calcium and other inorganic ions. These receptors and transporters include the inorganic phosphate transporter NaPi-IIb, and the transporter DMT1 (also known as NRAMP2, DCT1) for Fe2+, Mn2+, Ni2+, Co2+. The calcium sensing receptor (CaSR) is expressed in epithelial cells throughout the small and large intestine. Antibodies specific for CaSR and for other receptors for inorganic ions can be used to treat diseases or disorders of one or more of the following types: those characterized by abnormal inorganic ion homeostasis; those characterized by an abnormal amount of an extracellular or intracellular messenger whose production can be affected by inorganic ion receptor activity; those characterized by an abnormal effect of stimulation through the inorganic ion receptor (e.g., a different effect in kind or magnitude) levels, for example, as assessed by bone mineral density measurements; those characterized by an abnormal absorption of dietary calcium or other inorganic ions. The abnormal increase or decrease in these different aspects of inorganic ion homeostasis is relative to that occurring in the general population and is generally associated with a disease or disorder. Diseases and disorders characterized by abnormal inorganic ion homeostasis can be due to different cellular defects such as a defective inorganic ion receptor activity or a defective intracellular protein acted on by a receptor for an inorganic ion. Patients in need of treatment involving modulation of inorganic ion receptors can be identified using standard techniques known to those in the medical profession. Preferably, a patient is a human having a disease or disorder characterized by one or more of the following: (1) abnormal inorganic ion homeostasis, more preferably abnormal calcium homeostasis; (2) an abnormal level of a messenger whose production or secretion is affected by inorganic ion receptor activity, more preferably affected by calcium receptor activity; and (3) an abnormal level or activity of a messenger whose function is affected by inorganic ion receptor activity, more preferably affected by calcium receptor activity. In one embodiment of this invention, antibodies that enhance the activity of CaSR are used to modulate secretion and absorption of electrolytes, this being used in the treatment of diarrheal disease.

The GI tract contains proteinase-activated receptors (PARs), receptors that are activated by proteinases involved in digestion and host defense. Both PAR-1 and PAR-2 are expressed on intestinal epithelial cells. Intestinal PARs are involved in regulation of cell proliferation, inflammation and chloride secretion. Among the conditions to be treated using antibodies to PARs are characterized by inappropriate expression or activity of PARs such as when the PAR expression or activity level is too high or too low. Specific medical conditions that are treatable or preventable using antibodies to PARs include the treatment or prevention of cancers of the GI tract, treatment of secretory disorders or disorders associated with abnormal calcium secretion or absorption, or inflammatory diseases of the GI tract including, but not limited to: celiac disease, Crohn's disease; ulcerative colitis; idiopathic gastroparesis; inflammatory bowel disease and ulcers, including gastric and duodenal ulcers.

The GI tract contains receptors for bile acids. Bile acids undergo passive absorption in the proximal small intestine and active transport in the terminal ileum. Active transport is mediated by the apical sodium co-dependent bile acid transporter (ASBT) localized to the distal one-third of the ileum. An equilibrium generally exists between hepatic cholesterol and the bile acid pool Inhibition of ileal ASBT by oral administration of a specific antibody interrupts enterohepatic recirculation of bile acids, resulting in a decrease in the liver bile acid pool. This stimulates increased hepatic synthesis of bile acids from cholesterol, eventually depleting the liver's pool of esterified cholesterol, increasing the de novo synthesis of cholesterol in hepatocytes and increasing the uptake of serum cholesterol by upregulating the number of cell surface low density lipo-protein cholesterol receptors ("LDL receptors"). The number of hepatic LDL receptors directly impacts serum low density lipoprotein ("LDL") cholesterol levels, with an increase in the number of LDL receptors resulting in a decrease in serum cholesterol. The net result, therefore, is that serum LDL cholesterol levels decrease when intestinal bile acid reabsorption is reduced.

The GI tract contains cell surface peptidases and saccharases. Oral administration of antibodies specific for saccharases may be used in the treatment of diabetes, hyperlipaemia and adiposity, and in animal nutrition, for the better utilization of feed and for influencing the lean meat/fat ratio in favor of the proportion of lean meat.

The GI tract also contains receptors for cytokines, chemokines and other related immune mediators. Such receptors include receptors specific for inflammatory cytokines such as TNF-alpha, TNF-Kappa, IL-6, IFN-gamma, IL-1 beta, IL-12, IL-13, 11-23, and IL-2. Targeting any one or more of these receptors expressed in the lumen with an orally administered therapeutic antibody is useful for the treatment of a number of conditions modulated by these receptors including but not limited to irritable bowel syndrome, including Crohn's disease, ulcerative colitis, necrotizing enterocolitis, celiac disease, inflammation due to infection with invasive organisms such as *Salmonella* and *Escherichia coli*, or inflammation secondary to injury caused by surgery, trauma, ionizing radiation, or toxic chemicals, including NSAIDs.

Cancers of the GI tract are composed of cells that express receptors in the lumen of the GI tract that may be modulated by antibodies to inhibit the growth of the tumor and/or to kill the tumor. This invention encompasses antibodies that are directed against GI tumors, preferably colon cancers. Targets include MS412, PMEPA1, EGFR, CXCR2, VEGFR, PAR-1, CCK2R, TMPRS54, NMB-R, Neuropilin-1 (NRP-1), GLUT1, STIM1, and the voltage-gated L-type calcium channel alpha(1C), most preferably EGFR.

The terms "antibody" or "antibodies" as used herein refer to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding to a target receptor. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases that are able to compete with the intact antibody for specific binding, unless otherwise specified herein. Thus, for example, pepsin digests an antibody below the disulfide linkages in the hinge region to produce F(ab)'$_2$, a dimer of Fab which itself is a light chain joined to $V_{H-C_H}1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term "antibody", as used herein, also includes antibody fragments either produced by the modification of whole antibodies, or those synthesized de novo using chemical or recombinant DNA methodologies (e.g., single chain Fv, complementarity determining region (CDR) fragments, or polypeptides that contain at least a portion of an immunoglobulin that is sufficient to confer specific receptor binding to the polypeptide) or those identified using phage display libraries (see, e.g., McCafferty et al., *Nature* 348: 552-554 (1990)).

The terms "monoclonal antibody" or "monoclonal antibodies" as used herein refer to a preparation of antibodies of single molecular composition. A monoclonal antibody composition displays a single binding specificity and affinity for a particular epitope of a target receptor.

An "epitope" is the portion of a molecule that is bound by an antibody. An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody).

The term "polyclonal antibody" as used herein refers to a composition of different antibody molecules which is capable of binding to or reacting with several different specific antigenic determinants on the same or on different antigens. The variability in antigen specificity of a polyclonal antibody is located in the variable regions of the individual antibodies constituting the polyclonal antibody, in particular in the complementarity determining regions (CDR)1, CDR2 and CDR3 regions. Preferably, the polyclonal antibody is prepared by immunization of an animal with the target receptor or portions thereof as specified below. Alternatively, the polyclonal antibody may be prepared by mixing multiple monoclonal antibodies (e.g. Nowakowski, A. et al. 2002. Proc Natl Acad Sci USA 99, 11346-11350 and U.S. Pat. No. 5,126,130) having desired specificity to a target receptor.

Polyclonal antibody preparations isolated from the blood, milk, colostrum or eggs of immunized animals typically include antibodies that are not specific for the immunogen in addition to antibodies specific for the target receptor. Antibodies specific for the target receptor may be purified from the polyclonal antibody preparation or the polyclonal antibody preparation may be used without further purification. Thus, the term "polyclonal antibody" as used herein refers both to antibody preparations in which the antibody specific for the target receptor has been enriched and to preparations that are not purified. Numerous techniques are known to those in the art for enriching polyclonal antibodies for antibodies to specific targets. Recently a technology for recombinant production of highly specific polyclonal antibodies suitable for prophylactic and therapeutic administration has been developed (WO 2004/061104). The recombinant polyclonal antibody (rpAb) can be purified from a production bioreactor as a single preparation without separate handling, manufacturing, purification, or characterization of the individual members constituting the recombinant polyclonal protein.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. See, e.g., U.S. Pat. No. 4,816,567 and Morrison, 1985, *Science* 229:1202-07.

The invention further contemplates the use of molecules intended to mimic antibodies, such as aptamers. The invention also contemplates the use of "fusion proteins" in which a portion of an antibody molecule is fused to the ligand for the target receptor and thereby made specific for the target receptor. In another aspect, the present invention provides a derivative of an antibody specific for a target apical intestinal receptor. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Derivitized antibodies are also suitable for in-vivo or in-vitro detection of expression of a target receptor. In one preferred embodiment, an antibody derivitized with a physiologically acceptable label detectable by standard imaging equipment such as ultrasound, is used for in-vivo diagnostic imaging to detect aberrant expression of a target receptor. Such diagnostic techniques are useful in identifying patients who have elevated expression, activation or activity of a target receptor associated with one or more diseases thereby identifying patients who may benefit most from treatment with an antibody of the invention.

The present invention further comprises nucleic acid molecules encoding all or a part of an antibody of the invention, for example, one or both chains of the antibody of the invention or a fragment, derivative, or variation thereof. The nucleic acids can be single-stranded or double stranded and can comprise RNA and/or DNA nucleotides or variants there of such as peptide nucleic acids. The present invention further comprises host cells into which a recombinant expression vector or transfectoma is introduced and is capable of expressing an antibody of the invention or fragment thereof. A host cell can be any prokaryotic cell or eukaryotic cell. Vector DNA can be introduced into a host cell via conventional transformation or transfection techniques.

In one embodiment, the antibody of the invention is capable of at least partially blocking at least one biological activity of a target apical intestinal receptor. In another embodiment, the antibody of the invention has a binding affinity ($K_a$) for the target receptor of at least $10^6$. In other embodiments, the antibody exhibits a $K_a$ of at least $10^7$, at least $10^8$, at least $10^9$, or at least $10^{10}$. In another embodiment, the present invention provides an antibody that has a low dissociation rate from a target receptor. In one embodiment, the antibody has a $K_{off}$ of $1\times10^{-4}s^{-1}$ or lower. In another embodiment, the $K_{off}$ is $5\times10^{-5}s^{-1}$ or lower. It is understood by those skilled in the art that these affinities and dissociation rates refer to average affinities and dissociation rates when used to describe polyclonal antibodies. It is further understood by those skilled in the art that affinity is defined broadly and includes avidity as well as affinity. In another aspect, the present invention provides an antibody that inhibits at least one biological activity of a target receptor, for example, an antibody to the PAR-2 receptor may inhibit Ca2+mobilization. In one embodiment, the antibody has an $IC_{50}$ of 1000 nM or lower. In another embodiment, the $IC_{50}$ is 100 nM or lower; in another embodiment, the $IC_{50}$ is 10 nM or lower.

In one embodiment, monoclonal antibodies are preferred. In another embodiment polyclonal antibodies are preferred. Monoclonal antibodies are more controllable, but their specificity is limited. Polyclonal antibodies are more difficult to characterize, but their broad specificity means that they can interfere with target receptors in several different ways. In addition, the manufacture of polyclonal antibodies can be very inexpensive.

Methods of producing polyclonal and monoclonal antibodies that react specifically with the target receptors of the invention are known to those of skill in the art (see, e.g., Coligan, *Current Protocols in Immunology* (1991); Harlow & Lane, Antibodies, A Laboratory Manual (1988); Goding, *Monoclonal Antibodies: Principles and Practice* (2d ed. 1986); and Kohler & Milstein, *Nature* 256:495-497(1975). Such techniques include antibody preparation by selection of antibodies from libraries of recombinant antibodies in phage or similar vectors, as well as preparation of polyclonal and monoclonal antibodies by immunizing suitable animals (see, e.g., Huse et al., *Science* 246: 1275-1281 (1989); Ward et al., *Nature* 341: 544-546 (1989)).

A number of immunogens comprising target receptors or portions of target receptors may be used to produce antibodies specifically reactive with the target receptor. For example, an antigenic fragment or protein portion of a target receptor can be isolated using known procedures. Recombinant protein can be expressed in eukaryotic or prokaryotic cells as described above, and purified as generally described above. Alternatively, a synthetic peptide derived from a target receptor can be used as an immunogen. Preferably, the peptide is derived from a portion of the target receptor that is expressed extracellularly. The synthetic peptide may be conjugated to a carrier protein prior to immunization. Naturally occurring protein may also be used either in pure or impure form. The product is then injected into an animal capable of producing antibodies. Animals may also be immunized with cells that have been transfected with the target receptor or may be immunized with DNA encoding the target receptor. Either monoclonal or polyclonal antibodies may be generated accordingly.

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol., 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246: 1275-1281 (1989).

Methods of production of polyclonal antibodies are known to those of skill in the art. An appropriate animal is immunized with the protein using a standard adjuvant, such as Freund's adjuvant, and a standard immunization protocol. The animal's immune response to the immunogen preparation may be monitored by taking test bleeds and determining the titer of reactivity to target receptor. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Alternatively, eggs can be collected from immunized birds and antibody is isolated from the yolks of the eggs. Alternatively, milk or colostrum can be collected from immunized female animals and antibody is isolated from the milk or colostrum.

In one embodiment the antibody is isolated from the yolk of eggs from a bird such as a chicken, duck, or goose that has been immunized with a target receptor and/or peptide or antigenic portion derived from a target receptor and a suitable adjuvant. In another embodiment, the antibody is isolated from the serum of an animal such as a cow, horse, rabbit, or goat that has been immunized with a sweet taste receptor and/or peptide derived from a sweet taste receptor and a suitable adjuvant.

In one embodiment, the antibody is a polyclonal antibody derived from milk or colostrum. In one embodiment, the polyclonal antibody is derived from the milk or colostrum of a ruminant such as a cow, goat, sheep, camel or water buffalo. In another embodiment, the antibody is isolated from the milk or colostrum of a human. In a preferred embodiment, the polyclonal antibody is isolated from the milk or colostrum of a bovine, preferably an immunized cow. Bovine colostrum (early milk) is a preferred source of antibodies for this invention. In cows, antibody does not cross the placenta, and thus all passive immunity is transferred to the newborn calf through the milk. As a result, cows secrete a large bolus of antibody into the colostrum immediately after parturition and approximately 50% of the protein in colostrum is immunoglobulin. In the first 4 hours after birth, immunoglobulin concentrations of 50 mg/ml are typically found in the colostrum {Butler and Kehrli, 2005, Mucosal Immunology, 1763-1793}, dropping to 25-30 mg/ml 24 hours later {Ontsouka et al., 2003, J Dairy Sci, 86, 2005-11}. Colostrum and milk are a uniquely safe source of polyclonal antibody for oral delivery. There is already extensive human exposure to bovine immunoglobulin, as regular milk contains 1.5 g/L IgG.

In one aspect, the invention provides methods of treating a patient using the therapeutic compositions of the invention. The term "patient" as used herein refers to an animal. Preferably the animal is a mammal. More preferably the mammal is a human. A "patient" also refers to, for example, dogs, cats, horses, cows, pigs, guinea pigs, fish, birds and the like. Thus, the compositions and methods of the invention are equally suitable for veterinary treatments.

The terms "treatment" "treat" and "treating" encompasses alleviation, cure or prevention of at least one symptom or other aspect of a disorder, disease, illness or other condition (collectively referred to herein as a "condition"), or reduction of severity of the condition, and the like. A composition of the invention need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. In one embodiment, an indication that a therapeutically effective amount of a composition has been administered to the patient is a sustained improvement over baseline of an indicator that reflects the severity of the particular disorder.

In one embodiment, the invention provides a method of treating a condition comprising administering directly to the G.I. tract of a patient, a composition comprising an antibody specific for a target apical intestinal receptor as described above wherein the target receptor modulates a condition including, but not limited to: a metabolic condition, inflammation, cancer, drug overdose or toxicity, conditions modulated by receptors for neurotransmitters located on the luminal surface of the G.I. tract, and conditions modulated by receptors for inorganic ions.

The pharmaceutical compositions of the present invention comprise a therapeutically effective amount of an antibody of the present invention formulated together with one or more pharmaceutically acceptable carriers or excipients. By a "therapeutically effective amount" of an antibody of the invention is meant an amount of the composition which confers a therapeutic effect on the treated subject, at a reasonable benefit/risk ratio applicable to any medical treatment. The therapeutic effect is sufficient to "treat" the patient is that term is used herein.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention are administered directly to the G.I. tract of a patient. As used herein the phrase "administered directly to the G.I. tract of a patient" means oral or rectal administration. Thus the pharmaceutical compositions of the invention are appropriately formulated for administration directly to the G.I. tract of the patient such that they are suitable for oral or rectal administration to the patient.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound. In one embodiment, compositions for rectal administration are in the form of an enema.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

Oral delivery of protein therapeutics is challenging because the GI tract is designed to degrade and digest ingested material. However, bovine immunoglobulin is partially stable to gastric digestion. Several studies have directly examined the stability of bovine immunoglobulin in the human GI tract. Human subjects have been administered oral preparations of bovine colostral immunoglobulin and material has been recovered in ileal fluid effluent {Roos et al., 1995, J Nutr, 125, 1238-44; Warny et al., 1999, Gut, 44, 212-7}. Both intact IgG and functional activity were recovered in the ileum, with quantities ranging from 19% to 49%. Immunoglobulin has also been recovered in the stool of patients dosed with bovine IgG {McClead et al., 1988, Am J Med, 85, 811-6; Kelly et al., 1997, Antimicrob Agents Chemother, 41, 236-41}. Recovery rates ranged from 0.6% to 8.8% of the administered dose. The ability of bovine IgG to survive digestion by gastric and pancreatic proteases as well as the microbial proteases found in the colon highlights the unusual stability of these immunoglobulins.

Should it be desirable to avoid gastric degradation, there are many options for enteric coating (see for example U.S. Pat. Nos. 4,330,338 and 4,518,433). In one embodiment, enteric coatings take advantage of the post-gastric change in pH to dissolve a film coating and release the active ingredient. Coatings and formulations have been developed to deliver protein therapeutics to the small intestine and these approaches could be adapted for the delivery of an antibody of the invention. For example, an enteric-coated form of insulin has been developed for oral delivery {Toorisaka et al., 2005, J Control Release, 107, 91-6}.

In addition, the solid dosage forms of tablets, dragees, capsules, pills, and granules can be prepared with other coatings and shells well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes.

Antibodies that are directly engineered or modified to improve gastric stability would be preferred for use in this invention. Such engineering and modification could be accomplished by the addition or removal of glycosylation sites, by the addition of agents such as polyethylene glyclol, by the removal or modification of sites that confer acid instability, or by the removal or modification of sites that confer sensitivity to proteases present in the stomach and small intestine, including pepsin, trypsin and chymotrypsin.

Effective doses will vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the timing of delivery of the compound relative to food intake; the duration of the treatment; drugs used in combination or contemporaneously with the specific compound employed; and like factors well known in the medical arts.

Particular embodiments of the present invention involve administering a pharmaceutical composition comprising an antibody specific for a target receptor at a dosage of from about 1 mg per day to about 1 g/day, more preferably from about 10 mg/day to about 500 mg/day, and most preferably from about 20 mg/day to about 100 mg/day, to a subject. In one embodiment, a polyclonal antibody preparation is administered at a dosage of antibody from about 100 mg to about 50 g/day, more preferably from about 500 mg/day to about 10 g/day, and most preferably from about 1 g/day to about 5 g/day, to a subject, wherein the polyclonal antibody preparation has not been enriched for antibodies specific for the target receptor.

Treatment regimens include administering an antibody composition of the invention one time per day, two times per day, or three or more times per day, to treat a medical disorder disclosed herein. In one embodiment, an antibody composition of the invention is administered one time per week, two times per week, or three or more times per week, to treat a medical disorder disclosed herein.

The methods and compositions of the invention include the use of an antibody of the invention in combination with one or more additional therapeutic agents useful in treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antibody of the invention is administered at least once during a course of treatment that involves administering at least one other therapeutic agent to the patient.

The pharmaceutical compositions of this invention can be administered orally to animals, for example, by blending said pharmaceutical compositions into animal feed or said pharmaceutical compositions may be dissolved in water that the animals drink. The dosage for the treatment of an animal differs depending upon the purpose of administration (prevention or cure of disease) and type of administration and of the animal to be treated. Generally, a dosage of 1-1000 mg, preferably 20-100 mg, per kg of body weight of the animal may be administered per day, either at one time or divided into several times. It will be recognized that the above-specified dosage is only a general range which may be reduced or increased depending upon the age, body weight, condition of disease, etc. of the animal.

The following prophetic examples are provided for the purpose of illustrating specific embodiments or features of the invention and are not intended to limit its scope.

EXAMPLES

Example 1

Generation of Bovine Immunoglobulin Specific for GLUT2

The GLUT2 peptide derived from the extracellular loop between transmembrane regions 1 and 2 (aa 40-55) is synthesized with an additional cysteine residue at the C-terminus (SHYRHVLGVPLDDRRAC) (SEQ ID NO: 1) and coupled to maleimide activated mcKLH (Pierce Protein Research Products) using procedures supplied by the manufacturer.

The GLUT2-KLH conjugate is dissolved in PBS at 0.1 mg/mL and emulsified 1:1 (vol/vol) with EMULSIGEN®-D (purchased from MVP Laboratories, Omaha, Nebr.), an oil-in-water adjuvant containing an immunostimulant. Pregnant, healthy, mastitis-free Holstein dairy cows are immunized subcutaneously in the rear thigh with 100 µg of gliadin in a total volume of 2 mL. All vaccinations are performed under the direction of a licensed veterinarian and health records are maintained. Vaccinations are given on days 0, 21 and 35. The immunizations are timed such that the final boost is given approximately three weeks before parturition.

Colostrums are collected on days 1-4 after parturition. Colostrum is collected from each vaccinated cow separately and immediately frozen. Small (15 mL) samples of each milking are taken from cows prior to freezing bulk colostrum. These samples are used to measure immunogenicity of the vaccine regimen on an individual cow basis. Colostrums are pooled and frozen at −20° C. until further use.

Colostral whey is prepared using standard methods {Su and Chiang, 2003, J Dairy Sci, 86, 1639-45}. Samples from individual animals are processed independently. Colostrum collected on days 1-4 post-parturition is thawed and pooled. Colostrum is centrifuged at 4000×g to remove fat. The pH is slowly adjusted to 4.6 using 1 N HCl, incubated for 30 min at 37° C. to precipitate casein, and centrifuged. Whey is stored at −20° C.

The titer of anti-GLUT2 antibody in each whey sample is assessed by ELISA. Microtiter plates are coated with GLUT2-BSA conjugates, prepared as above, at 1 µg/ml and blocked with 1% ovalbumin. Serial dilutions of colostral whey are added to the plates in triplicate wells and incubated for 1 hr at room temperature. Plates are washed and developed with horseradish peroxidase (HRP)-labeled sheep anti-bovine IgG (h+1) (Bethyl Laboratories, Montgomery, Tex.) and substrate OPD using standard techniques. The second antibody will recognize all bovine immunoglobulin isotypes through detection of the light chain. Colostral whey from cows immunized with influenza is used as a negative control. Antibody levels are expressed as titer, the reciprocal of the dilution yielding a half-maximal absorbance in the ELISA. Antibodies specific for GLUT2 are generated by immunization with the GLUT2 peptide conjugate, as demonstrated by a positive response in the ELISA using colostrum from immunized cows but not from cows immunized with influenza.

The concentration of immunoglobulin in each whey sample is also determined by ELISA. ELISA plates are coated with sheep anti bovine IgG (h+1) (Bethyl Laboratories) and blocked with 1% ovalbumin. Serial dilutions of whey are added to the plates and developed as in the anti-TNF ELISA above. Purified bovine immunoglobulin is used as a control. The specific activity of each colostral sample is calculated (titer per mg immunoglobulin). A pool is created from all colostral samples that contain levels of anti-GLUT2 antibody more than 2× above background and used for all subsequent work.

Example 2

Generation of Bovine Immunoglobulin Specific for GLUT5

The GLUT5 peptide derived from the extracellular loop between transmembrane regions 1 and 2 (aa 62-77) is synthesized with an additional cysteine residue at the C-terminus (LLMQQFYNETYYGRTC) (SEQ ID NO: 2) and coupled to maleimide activated mcKLH (Pierce Protein Research Products) using procedures supplied by the manufacturer.

The GLUT5-KLH conjugate is dissolved in PBS at 0.1 mg/mL and emulsified 1:1 (vol/vol) with CARBIGEN® (purchased from MVP Laboratories, Omaha, Nebr.), a carbomer-based adjuvant. Pregnant, healthy, mastitis-free Holstein dairy cows are immunized subcutaneously in the rear thigh with 100 µg of the GLUT5-KLH conjugate in a total volume of 2 mL. All vaccinations are performed under the direction of a licensed veterinarian and health records are maintained. Vaccinations are given on days 0, 21 and 35. The immunizations are timed such that the final boost is given approximately three weeks before parturition.

Colostrums are collected on days 1-4 after parturition. Colostrum is collected from each vaccinated cow separately and immediately frozen. Small (15 mL) samples of each milking are taken from cows prior to freezing bulk colostrum. These samples are used to measure immunogenicity of the vaccine regimen on an individual cow basis. Colostrums are pooled and frozen at −20° C. until further use.

Colostral whey is prepared using standard methods {Su and Chiang, 2003, J Dairy Sci, 86, 1639-45}. Samples from individual animals are processed independently. Colostrum collected on days 1-4 post-parturition is thawed and pooled. Colostrum is centrifuged at 4000×g to remove fat. The pH is slowly adjusted to 4.6 using 1 N HCl, incubated for 30 min at 37° C. to precipitate casein, and centrifuged. Whey is stored at −20° C.

The titer of anti-GLUT5 antibody in each whey sample is assessed by ELISA. Microtiter plates are coated with GLUT5-BSA conjugates, prepared as above, at 1 µg/ml and blocked with 1% ovalbumin. Serial dilutions of colostral whey are added to the plates in triplicate wells and incubated for 1 hr at room temperature. Plates are washed and developed with horseradish peroxidase (HRP)-labeled sheep anti-bovine IgG (h+1) (Bethyl Laboratories, Montgomery, Tex.) and substrate OPD using standard techniques. The second antibody will recognize all bovine immunoglobulin isotypes through detection of the light chain. Colostral whey from cows immunized with influenza is used as a negative control. Antibody levels are expressed as titer, the reciprocal of the dilution yielding a half-maximal absorbance in the ELISA. Antibodies specific for GLUT5 are generated by immunization with the GLUT5 peptide conjugate, as demonstrated by a positive response in the ELISA using colostrum from immunized cows but not from cows immunized with influenza.

Example 3

Generation of Bovine Immunoglobulin Specific for GLUT7

The GLUT7 peptide derived from the extracellular loop between transmembrane regions 1 and 2 (aa 50-77) is synthesized with an additional cysteine residue at the C-terminus (KVGTSCGWGNVFQVFKSFYNETYFERHC) (SEQ ID NO: 3) and coupled to maleimide activated ovalbumin (Pierce Protein Research Products) using procedures supplied by the manufacturer.

The GLUT7-OVA conjugate is dissolved in PBS at 0.2 mg/mL and emulsified 1:1 (vol/vol) with the adjuvant EMULSIGEN-D® (purchased from MVP Laboratories, Omaha, Nebr.). Pregnant, healthy, mastitis-free Holstein dairy cows are immunized subcutaneously in the rear thigh with 200 µg of the GLUT7-OVA conjugate in a total volume of 2 mL. All vaccinations are performed under the direction of a licensed veterinarian and health records are maintained. Vaccinations are given on days 0, 21 and 35. The immunizations are timed such that the final boost is given approximately three weeks before parturition.

Colostrums are collected on days 1-4 after parturition. Colostrum is collected from each vaccinated cow separately and immediately frozen. Small (15 mL) samples of each milking are taken from cows prior to freezing bulk colostrum.

These samples are used to measure immunogenicity of the vaccine regimen on an individual cow basis. Colostrums are pooled and frozen at −20° C. until further use.

Colostral whey is prepared using standard methods. Samples from individual animals are processed independently. Colostrum collected on days 1-4 post-parturition is thawed and pooled. Colostrum is centrifuged at 4000×g to remove fat. The pH is slowly adjusted to 4.6 using 1 N HCl, incubated for 30 min at 37° C. to precipitate casein, and centrifuged. Whey is stored at −20° C.

The titer of anti-GLUT7 antibody in each whey sample is assessed by ELISA. Microtiter plates are coated with GLUT7-KLH conjugates, prepared as above, at 1 µg/ml and blocked with 1% immunoglobulin-free BSA. Serial dilutions of colostral whey are added to the plates in triplicate wells and incubated for 1 hr at room temperature. Plates are washed and developed with horseradish peroxidase (HRP)-labeled sheep anti-bovine IgG (h+l) (Bethyl Laboratories, Montgomery, Tex.) and substrate OPD using standard techniques. The second antibody will recognize all bovine immunoglobulin isotypes through detection of the light chain. Colostral whey from cows immunized with influenza is used as a negative control. Antibody levels are expressed as titer, the reciprocal of the dilution yielding a half-maximal absorbance in the ELISA. Antibodies specific for GLUT7 are generated by immunization with the GLUT7 peptide conjugate, as demonstrated by a positive response in the ELISA using colostrum from immunized cows but not from cows immunized with influenza.

Example 4

Antibody Inhibition of GLUT7-Mediated Uptake of Glucose

Anti-GLUT7 antibody is generated as described in Example 3 and used to inhibit glucose uptake by Xenopus oocytes expressing GLUT7. Plasmid containing the hGLUT gene is produced and transcribed as described {Li et al., 2004, Am J Physiol Gastrointest Liver Physiol, 287, G236-42}. Stage V/VI oocytes are harvested from anesthetized *Xenopus laevis* and placed in Modified Barth's Medium (MBM). The follicular layer is removed by treatment for 2 h with 0.02 g/ml type I collagenase (Sigma Aldrich), followed by hypertonic phosphate treatment. Oocytes are incubated at 16-18° C. for 24 hr in MBM and injected with 20 ng GLUT7 synthetic mRNA transcript and incubated for 3-5 days at 16-18° C. before use in functional uptake assays. Control oocytes are injected with water alone.

Uptake experiments are performed at 20° C. with 5-10 oocytes for each condition. GLUT7-transfected or control oocytes are preincubated for 30 min with varying doses of GLUT7-specific antibody or control influenza-specific bovine antibody. Three doses are examined: the dose that generates a half-maximal response in a GLUT7-specific ELISA, and doses 10-fold higher and 10-fold lower. [3H] glucose (100 uM, 1 uCi/ml) is added and incubated for an additional 30 min. Oocytes are washed with cold MBM to stope the incubation and individual oocytes are placed in vials and dissolved in 0.5 ml 5% SDS for 30 min. Scintillation fluid is added to each vial and radioactivity measured. Data are expressed as pmoles glucose taken up over 30 min. Reduced levels of glucose uptake are seen in the presence of GLUT7-specific antibody than in the controls.

Example 5

Antibody Inhibition of Glucose Uptake by GLUT2-Specific Antibody

Male Wistar rats (240-270 g) are anesthetized using an ip injection of Hypnorm and Hypnovel. A mid to distal loop of jejumum is cannulated at 10 and 35 cm from the Ligament of Treitz and perfused in vivo in a single-pass mode with perfusate comprising nutrient at the stated concentration in modified Krebs-Henseleit buffer (KHB) containing 201 mM NaCl, 4.5 mM KCl, 1.0 mM $MgSO_4$, 1.8 mM $Ha_2HPO_4$, 0.2 mM $NaH_2PO_4$, 1.25 mM $CaCl_2$ and 25 mM $NaHCO_3$, gassed to pH 7.4 with 19:1 $O_2$-$CO_2$ before use. The flow rate of perfusate is 0.37 ml/min and that of gas 0.19 ml/min. The jejunal loop is perfused with 20 mM glucose for 30 min and then switched to glucose mixed with GLUT2-specific antibody for an additional 30 min. Three concentrations of antibody are tested: the antibody concentration that generates a half-maximal response in a GLUT2-specific ELISA, and concentrations 10-fold higher and 10-fold lower. Glucose absorption rates are expressed as the rate of loss from the luminal perfusate expressed in umol/min (g dry weight)$^{-1}$. Reduced glucose absorption is seen in the presence of GLUT2-specific antibody when compared to controls.

Example 6

Generation of Bovine Immunoglobulin Specific for T1R3

Peptides are synthesized that are based on the extracellular domain of the sweet taste receptor T1R3 from either mouse (HEGLVPQHDTSCQQLGK) (SEQ ID NO: 4) or human (EEAGLRSRTRPSSP) (SEQ ID NO: 5). The peptides are dissolved in PBS at 0.1 mg/mL and emulsified 1:1 (vol/vol) with the adjuvant EMULSIGEN-D® (purchased from MVP Laboratories, Omaha, Nebr.). Pregnant, healthy, mastitis-free Holstein dairy cows are immunized subcutaneously in the rear thigh with 100 µg of the T1R3 peptides in a total volume of 2 mL. All vaccinations are performed under the direction of a licensed veterinarian and health records are maintained. Vaccinations are given on days 0, 21 and 35. The immunizations are timed such that the final boost is given approximately three weeks before parturition.

Colostrums are collected on days 1-4 after parturition. Colostrum is collected from each vaccinated cow separately and immediately frozen. Small (15 mL) samples of each milking are taken from cows prior to freezing bulk colostrum. These samples are used to measure immunogenicity of the vaccine regimen on an individual cow basis. Colostrums are pooled and frozen at −20° C. until further use.

Colostral whey is prepared using standard methods. Samples from individual animals are processed independently. Colostrum collected on days 1-4 post-parturition is thawed and pooled.

Colostrum is centrifuged at 4000×g to remove fat. The pH is slowly adjusted to 4.6 using 1 N HCl, incubated for 30 min at 37° C. to precipitate casein, and centrifuged. Whey is stored at −20° C.

The titer of anti-T1R3 antibody in each whey sample is assessed by ELISA. Microtiter plates are coated with the murine or human T1R3 peptide at 1 µg/ml and blocked with 1% ovalbumin. Serial dilutions of colostral whey are added to the plates in triplicate wells and incubated for 1 hr at room temperature. Plates are washed and developed with horseradish peroxidase (HRP)-labeled sheep anti-bovine IgG (h+l)

(Bethyl Laboratories, Montgomery, Tex.) and substrate OPD using standard techniques. Colostral whey from cows immunized with influenza is used as a negative control. Antibody levels are expressed as titer, the reciprocal of the dilution yielding a half-maximal absorbance in the ELISA. Antibodies specific for T1R3 are generated by immunization with T1R3, as demonstrated by a positive response in the ELISA using colostrum from immunized cows but not from cows immunized with influenza.

Example 7

Inhibition of GLP-1 Release by Antibodies Specific for T1R3

C57BL/6 mice (8 mice per group) are fasted overnight and administered glucose by gastric gavage (2 g/kg body weight) in the presence or absence of polyclonal bovine antibody specific for the murine T1R3 sweet taste receptor. The antibody dose is selected that is 10-fold higher than that calculated to bind 90% of the intestinal T1R3 receptors. An additional control group is administered bovine antibody isolated from non-immunized cows. Blood samples (0.1 ml) are collected immediately before and 10, 20 and 40 minutes after glucose administration. Dipeptidyl peptidase IV inhibitor is added to the blood samples upon collection. Blood samples are analyzed for the levels of glucose using a glucometer, for plasma insulin by ELISA (ALPCO Diagnostics, Salem, N.H.), and for plasma GLP-1 by ELISA (ALPCO Diagnostics). In the presence of antibody specific for T1R3, glucose dosing results in reduced levels of blood glucose, of plasma insulin and of plasma GLP-1 when compared to glucose dosing in the absence of antibody.

Example 8

Inhibition of LPS-induced Cytokine Production by Anti-TLR4 Antibody

An anti-TLR4 monoclonal antibody is generated by immunization of rats with the Ba/F3 cell line expressing mouse TLR4 and MD-2. Hybridomas are generated using standard techniques and cells secreting specific antibody are identified by the presence in the supernatant of antibody capable of binding to TLR4. Alternatively, anti-TLR4 monoclonal antibody is obtained from a commercial source, such as Imgenix. Murine splenocytes are cultured at $5 \times 10^5$ cells/ml with lipopolysaccharide (LPS) from *E. coli* at 100 ng/ml in the presence of varying concentrations of the anti-TLR4 monoclonal antibody. After 72 hr, supernatants are removed and assayed for the presence of TNFalpha using an ELISA kit. The anti-TLR4 antibody inhibits the production of LPS-induced cytokine production.

Example 9

Inhibition of Necrotizing Enterocolitis with Oral Anti-TLR4 Antibody

Necrotizing enterocolitis is induced in neonatal mice as described {Jilling et al., 2006, J Immunol, 177, 3273-82}. Briefly, C3HeB/FeJ or C3H/HeJ mouse pups are delivered by Cesarean section between E20-21. Pups are stabilized, dried and maintained in an incubator at 37 deg C., and bowel/bladder function are stimulated by a soft cotton-tip applicator every 3 h. Two hours after delivery, animals are fed Esbilac puppy formula by non-sanitized feeding orogastric catheter every 2 h starting with 0.03 ml, increasing to 0.04 ml in the subsequent 24 h to deliver approximately 200 kcal/kg/day. Asphyxia stress is accomplished by exposure to 100% nitrogen for 60 s, followed by exposure to cold (4 deg C.) for 10 min twice daily. Animals are euthanized at 72 h and intestines are collected in 10% formalin and processed for H&E staining Sections are analyzed and tissue injury scored from 1-4 by a blinded investigator using an established scoring system {Jilling et al., 2006, J Immunol, 177, 3273-82}.

To test the effect of an anti-TLR4 antibody on necrotizing enterocolitis, a monoclonal antibody specific for murine TLR4/MD2 is purchased from InvivoGen (San Diego, Calif.). Antibody is mixed with the Esbilac immediately prior to feeding at a dose of 1 ug/ml. Four groups of mice are compared: C3HeB/FeJ mice with and without antibody and C3H/HeJ mice with and without antibody. The incidence of necrotizing enterocolitis in the 4 groups is assessed. Antibody treatment reduces the incidence of necrotizing enterocolities in the C3HeB/FeJ mice, but has no effect on the C3H/HeJ mice (C3H/HeJ do not express TLR4).

Example 10

Generation of a Monoclonal Antibody that Inhibits the Apical Sodium-Dependent Bile Acid Transporter (ASBT)

Mice are immunized with 10 μg of a peptide derived from the extracellular loop EL1 of human ASBT (VVLIIGCCPG-GTASNILAYWVDGDMDLS) (SEQ ID NO: 6) in complete Freund's adjuvant and boosted at day 14 with the same peptide in incomplete Freund's adjuvant (IFA). An additional boost of antigen in IFA is given at day 28 and at day 35 the mice are sacrificed. Splenic B cells are fused with a myeloma line to produce B cell hybridomas using standard techniques. Supernatants from antibody-secreting hybridomas are screened for their ability to bind the immunizing peptide by ELISA. Positive antibodies are further screened for their ability to inhibit bile acid uptake in an in vitro system using the human intestinal Caco-2 cell line as described {Alrefai et al., 2005, Am J Physiol Gastrointest Liver Physiol, 288, G978-85}. Briefly, confluent Caco-2 cells are equilibrated at room temperature and then washed and incubated for 15 min at 25 deg C. with 110 mM NaCl, 4 mM KCl, 1 mM $MgSO_4$, 1 mM CaCl, 50 mM mannitol and 10 mM HEPES, pH 7.4 in the presence or absence of varying concentrations of the anti-ASBT antibody. Cells are washed and incubated with the same buffer and same antibody concentration with 10 uM 1(uCi/ml) of $^3$H-taurocholic acid. After 5 minutes, the transport process is stopped by washing the cells with ice cold PBS and solubilizing the cells with 0.5 N NaOH. Protein concentration is measured and uptake of [$^3$H]-taurocholic acid is expressed as picomole per milligram protein per 5 minutes Inhibitory antibody reduces the uptake of taurocholic acid by the apical sodium-dependent bile acid transporter (ASBT).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A pharmaceutical composition comprising an antibody specific for an apical intestinal receptor in the gastrointestinal tract of a patient, wherein the apical intestinal receptor is a sugar receptor or sugar transporter, wherein the pharmaceutical composition is formulated for direct delivery to the gastrointestinal (GI) tract of the patient, and wherein the antibody is derived from the milk or colostrum of a ruminant animal.

2. The pharmaceutical composition of claim 1, wherein the antibody is a polyclonal antibody isolated from milk or colostrum.

3. The pharmaceutical composition of claim 1, wherein the ruminant is a cow.

4. The pharmaceutical composition of claim 1, wherein the sugar receptor or transporter is selected from: sodium/glucose transporter-1 (SGLT1), glucose transporter-5 (GLUT5), glucose transporter-2 (GLUT2), glucose transporter-7 (GLUT7), sweet taste receptor-1 (T1R1), sweet taste Receptor-2 (T1R2), and sweet taste receptor-3 (T1R3).

5. The pharmaceutical composition of claim 4, wherein the sugar receptor or transporter is SGLT1.

6. A method of treating a metabolic disease in a patient comprising orally or rectally administering to the patient a therapeutically effective amount of the composition of claim 1.

7. The method of claim 6, wherein the metabolic disease is selected from: hyperglycemia, diabetes, impaired glucose tolerance, impaired fasting glycemia, obesity, hyperinsulinemia, hyperlipidemia, hyper-cholesterolemia, hypertriglyceridemia, lipid metabolism disorder, atherosclerosis, hypertension, congestive heart failure, edema, hyperuricemia, and gout.

8. The method of claim 7, wherein the treatment of diabetes includes complications associated with diabetes selected from: retinopathy, neuropath, nephropathy, ulcer, and macroangiopathy.

9. The method of claim 6, wherein the composition is administered before ingesting a substance that may contain glucose or concurrently with the ingestion of a substance that may contain glucose, fructose or a related hexose.

10. The method of claims 6, wherein the composition is administered after ingesting a substance that may contain glucose, fructose or a related hexose.

* * * * *